United States Patent [19]

Nagasaki et al.

[11] Patent Number: 4,593,313
[45] Date of Patent: Jun. 3, 1986

[54] ENDOSCOPE

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 647,200

[22] Filed: Sep. 4, 1984

[30] Foreign Application Priority Data

Sep. 5, 1983 [JP] Japan .................. 58-163586

[51] Int. Cl.⁴ ............................................. A61B 1/04
[52] U.S. Cl. .................................... 358/98; 128/6; 358/42
[58] Field of Search ............ 358/98, 1, 11, 21 R, 358/28, 29, 30, 42, 81, 82; 128/3, 4, 5, 6, 7, 8; 356/241

[56] References Cited

U.S. PATENT DOCUMENTS

| | | | |
|---|---|---|---|
| Re. 31,289 | 6/1983 | Moore | 358/98 |
| 3,558,806 | 1/1971 | Monahan | 358/30 |
| 4,308,551 | 12/1981 | Ohnuma | 358/29 |
| 4,353,093 | 10/1982 | Durbin | 358/21 R |
| 4,486,771 | 12/1984 | Machida | 358/29 |
| 4,532,918 | 8/1985 | Wheeler | 128/6 |
| 4,546,379 | 10/1985 | Sarofeen | 358/42 |

*Primary Examiner*—Howard W. Britton
*Attorney, Agent, or Firm*—Armstrong, Nikaido, Marmelstein & Kubovcik

[57] ABSTRACT

The endoscope equipment of this invention is to display on the monitor screen pictures of different wavelength regions with particular color signals and the synthesized picture and spectral analysis waveforms at particular points by sequentially irradiating the light of a specified wavelength region to a subject, receiving the image of the reflected light with the image pickup element, converting it into electrical signals, conducting spectral characteristic correction on the obtained signals, and then by processing the signals for each wavelength region.

6 Claims, 8 Drawing Figures

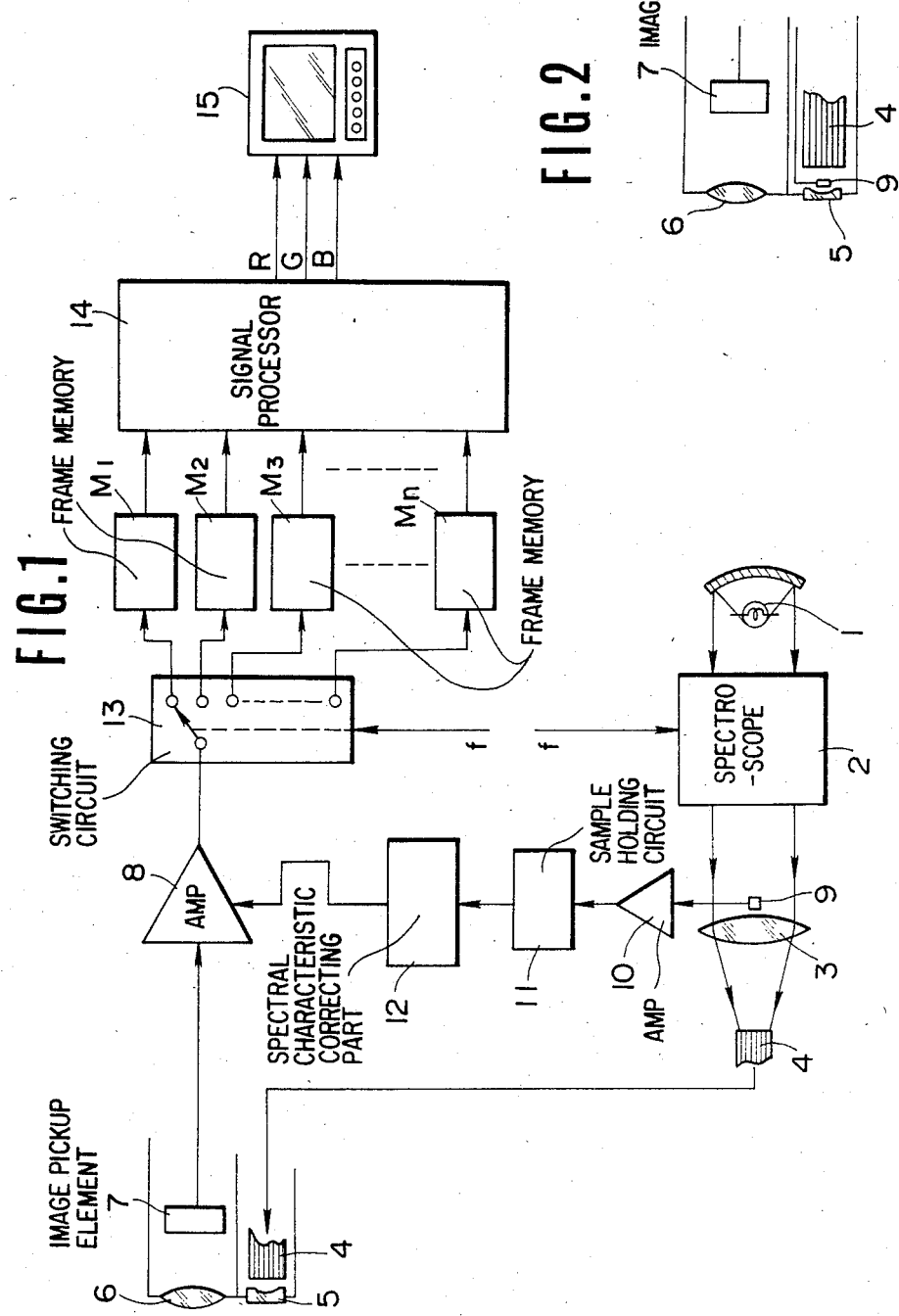

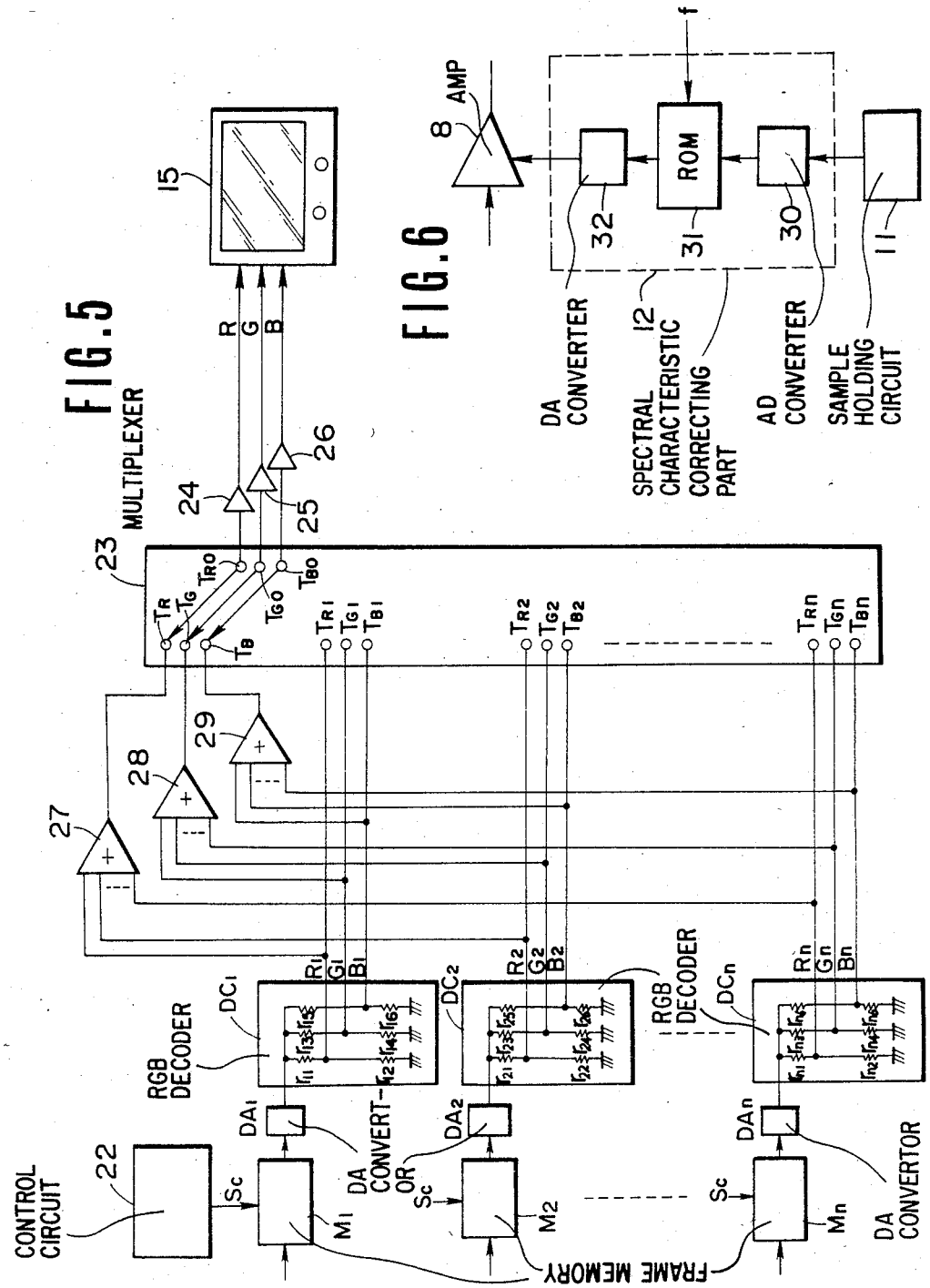
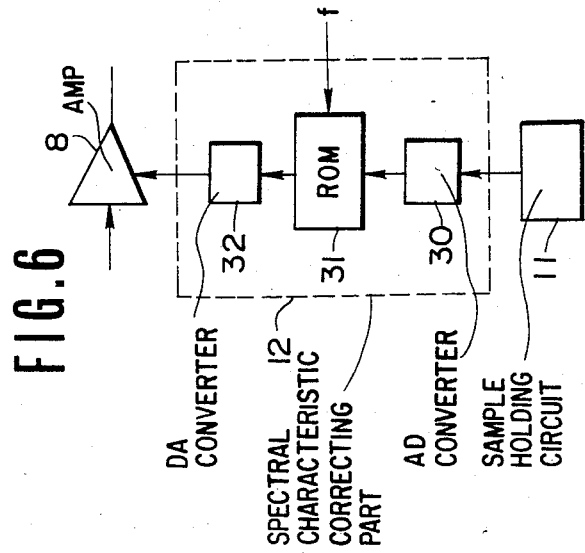

ENDOSCOPE

BACKGROUND OF THE INVENTION

This invention concerns an endoscope using an image pickup element which can separate the light from the light source into multiple various wavelength regions, irradiate them to a subject, correct the spectral characteristics of the image signals obtained by the image pickup element and display the picture in accordance with the wavelength region of the subject and waveform image analyzed.

Generally, the endoscope is used to observe inside the cavity of a living body or mechanical component.

Conventionally, in such an endoscope, the image of a subject is introduced out by means of the optical fiber bundle and the optical image formed on the irradiating end face of the optical fiber bundle is observed through the eye lens system. In another equipment already developed, an image pickup element such as charge coupled device (CCD) is provided at the end position of the axis of the endoscope in place of the above optical fibers and the optical image formed on the light receiving face of the image pickup element is converted into electrical signals, introduced out of the body cavity or component cavity through the signal line, and displayed on a television monitor after necessary signal processing. In such endoscope, the light source unit to illuminate the subject is usually installed outside the endoscope and the light from the light source unit is introduced to the end of the inserting member of the endoscope through the light source connection and light guide of the endoscope.

In the aforementioned endoscope, however, the light irradiated from the light source unit through the light guide includes the lights of various wavelength regions of 400–3000 nm and the information obtained from the subject also corresponds to the various wavelength regions, and therefore, it is impossible to observe restricting to a particular wavelength region.

That is, in the case of the former optical observation, the subject is observed directly with the naked eye through the optical lens, and therefore, the information obtained corresponds to the range of the visible wavelength region of the illuminating light, and in the case of the picture observation using the image pickup element, the image pickup element can sense the light in other regions than the visible ray wavelength such as infrared wavelength region and the information obtained corresponds to the range of the wavelength regions including such invisible ray wavelength.

By the way, if a part to be observed is an internal organ of man, the energy reflected or absorbed for each wavelength region of the light irradiated differs, for example, from stomach to blood. For example, in order to recognize a tissue similar to blood in the stomach or part which contains a lot of blood, the difference is more clearly seen by comparing them in the near infrared wavelength region.

Therefore, in the conventional endoscopes which observe in a wide wavelength range including the visible ray wavelength region, it required a high degree of knowledge and experience and a lot of time and labor to determine and recognize the difference between the affected part and normal part of the living body by means of the image observed.

BRIEF SUMMARY OF THE INVENTION

The objective of this invention is to provide an endoscope which can irradiate sequentially the separated light of various wavelength regions to a subject and display the image information in accordance with the wavelength regions and analyzed waveform image, in consideration of the aforementioned points.

Another objective of this invention is to provide an endoscope which can display the information by means of which the difference between the affected part and normal part, for example, in the observation of the inside of a living body can be easily determined.

Other features and benefits of this invention will be made clear by the following description.

BRIEF DESCRIPTION OF THE DRAWINGS

FIG. 1 is a block diagram to show one embodiment of the endoscope related to this invention.

FIG. 2 is a partial view of another embodiment of arrangement of the light receiving element shown in FIG. 1.

FIG. 5 is a block diagram to show in the concrete one example of the makeup of the signal processor shown in FIG. 1.

FIG. 6 is a block diagram to show in the concrete one example of the makeup of the spectral characteristic correcting part shown in FIG. 1.

DETAILED DESCRIPTION OF THE EMBODIMENTS

Figure 3:
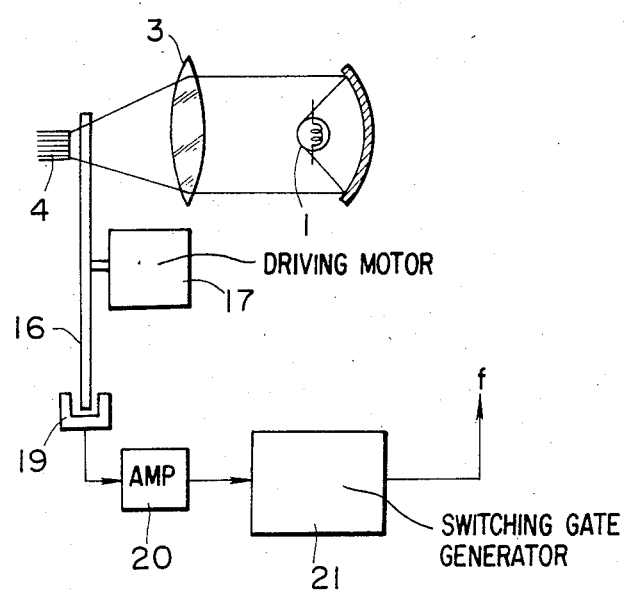
FIG. 3 is a block diagram to show in the concrete one example of the composition of the spectroscope shown in FIG. 1.

In FIG. 1, the endoscope equipment separates the light from the light source lamp 1 using the spectroscope 2, then converges the light of separated each wavelength region using the convergent lens 3, and irradiates it to a subject through the light guide 4 such as optical fiber bundle and the irradiating lens 5 at the end of the inserting member of the endoscope. The spectroscope 2 can separate the light of the wavelength from infrared rays to visible rays and ultraviolet rays radiated from the light source lamp 1 and switch and output the light in each wavelength region separated, synchronized with the frame switching signal f. Then the light reflected from the subject which was illuminated with the separated wavelength region light is received at the light receiving face of the image pickup element 7 through the image pickup lens 6 at the end of the inserting member of the endoscope, converted into electrical signals, and introduced into the variable gain amplifier (multiplier) 8. This amplifier 8 can automatically change the gain by means of the spectral characteristic correction signal and makes it possible to conduct the spectral analysis under constant illuminating conditions by correcting the difference in the intensity (amplitude) of the light separated into each wavelength region which occurs depending on the condition of the light source 1. That is, the light separated into each wavelength region by the spectroscope 2 (single spectral light) is received by the light receiving element 9 which has the same characteristics as the image pickup element 7, amplified by the amplifier 10, and then sample-held by the sample holding circuit 11, and on basis of the sample hold signal, the signal for correcting the spectral characteristics is prepared by the spectral characteristic correcting part 12 taking into consideration the correction amount for the light guide and optical lens system, and the correction signal and the image pickup signal from the image pickup element 7 are multiplied by the amplifier 8 to output the corrected signal. The signals from the amplifer 8 are switched by the switching circuit 13 and the image information for each wavelength region is sequentially accumulated in the multiple (n units) frame memories $M_1, M_2, M_3, \ldots, M_n$. The switching by the switching circuit 13 is done synchronized with the frame switching signal f as in the case of the switching by the spectroscope 2. The image signal of each wavelength region in the frame memories $M_1$-$M_n$ is read out for each memory, processed in the signal processor 14, and input to the monitor 15. For writing into the frame memories $M_1$-$M_n$ the signals are A/D converted into digital value and for reading out they are D/A converted into analog value. On the screen of the monitor 15 a picture of the wavelength region is displayed by means of the particular color signals. In such a case, in addition to the display of the picture of each wavelength region only, the combination of the pictures of various wavelength regions can also be displayed, and also the reflectance or absorption spectrum waveform of a particular place of the subject is displayed. To the monitor 15 the R (red), G (green) and B (blue) color signals are input to make it possible to display in color.

If the light receiving element 9 is placed between the irradiating lens 5 and light guide 4 on the end side of the inserting member of the endoscope as shown in FIG. 2, the signal for correcting the spectral characteristics with the spectral transmission characteristics of the light guide taken into consideration can be easily obtained.

Figure 4:
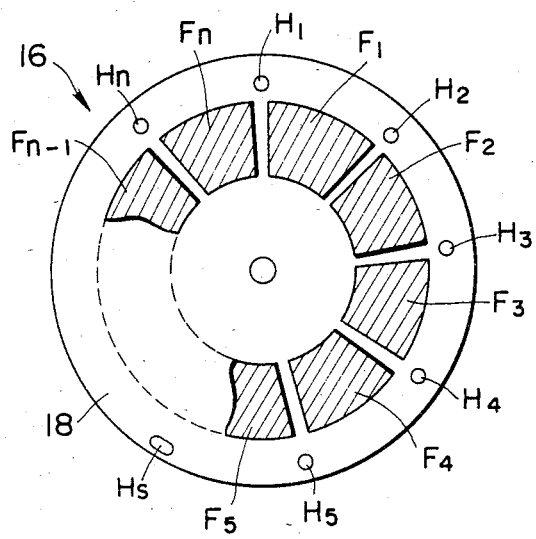
FIG. 4 is a front view to show the composition of the rotary filter shown in FIG. 3.

FIG. 3 shows in the concrete one example of makeup of the spectroscope 2 shown in FIG. 1. The light from the light source lamp 1 passes through the convergent lens 3 and enters the read end face of the light guide 4. Facing the rear end face of the light guide 4, a rotary filter 16 which can transmit the light for each wavelength region is provided. The rotary filter 16 can be rotated at a constant speed by means of the driving motor 17. The rotary filter 16 consists, as shown in FIG. 4, n spectral filters $F_1, F_2, \ldots F_n$ with different transmission wavelength regions arranged in a circular ring on the same circumference of the light shielding plate 18. The spectral filters $F_1$-$F_n$ can transmit particular wavelength regions from infrared rays to visible rays and ultraviolet rays and are arranged at light shielding intervals. On the same circumference near the periphery of the light shielding plate 18 the rotation position detecting holes $H_1, H_2, \ldots H_n$ are provided at the position to correspond to the light shielding region between the filters. Also the rotary filter 16 is provided with a start pulse detecting hole $H_s$ which detects one turn of said filter. Near the peripheral edge of the rotary filter 16, as shown in FIG. 3, the photo-interrupter 19 to detect the aforementioned rotation position detecting holes $H_1$-$H_n$ and the start pulse detecting hole $H_s$ is provided. As the photo-interrupter 19, for example, the photocoupler is used, and together with the amplifier 20 connected to the photo-interrupter 19, it forms the rotation position detector. As the rotary filter 16 rotates, the rotation position detector detects the aforementioned holes $H_1$-$H_n$ and the hole $H_s$ and inputs the detection signal to the switching gate generator 21. The switching gate generator 21 makes the frame switching signal f in accordance with the timing of the hole detection signal input and outputs it to the switching circuit 13 in FIG. 1.

Of the particular wavelength region spectral filters $F_1$-$F_n$ arranged on the rotary filter 16, for example, for the 3 filters $F_{n-2}$, $F_{n-1}$ and $F_n$, the R, G and B image pickup filters with the transmission bands for R, G, and B lights can be used to pick up the color image of one color of R, G or B or 3-color combination.

FIG. 5 shows in the concrete one example of the makeup of the signal processor 14 shown in FIG. 1. The image signals of each wavelength region stored in the frame memories $M_1$-$M_n$ are read out simultaneously by means of the control signal $S_C$ from the control circuit 22 and converted back into analog values by the DA converters $DA_1$-$DA_n$ connected to the memories $M_1$-$M_n$. The DA-converted image signals of each wavelength region are input to the RGB decoders $DC_1$-$DC_n$. The RGB decoders $DC_1$-$DC_n$ consist of 3 resistor division circuit each connected in parallel. For example, the $DC_1$ consists of series resistor circuit of resistors $r_{11}$ and $r_{12}$, series resistor circuit of resistors $r_{13}$ and $r_{14}$ and series resistor circuit of resistors $r_{15}$ and $r_{16}$ connected in parallel. $DC_n$ consists of series resistor circuit of resistors $r_{n1}$ and $n_{n2}$, series resistor circuit of resistors $r_{n3}$ and $r_{n4}$ and series resistor circuit of resistors $r_{n5}$ and $r_{n6}$ connected in parallel. And from the resistor division points of each series resistor circuit the R, G and B signals are taken out. For example, in the case of the decoder $DC_1$, from the connection point of resistors $r_{11}$ and $r_{12}$, $R_1$ signal is taken out, from the connection point of resistors $r_{13}$ and $r_{14}$, $G_1$ signal is taken out, and from the connection point of resistors $r_{15}$ and $r_{16}$, $B_1$ signal is taken out, and in the case of the decoder $DC_n$, from the connection point of resistors $r_{n1}$ and $r_{n2}$, $R_n$ signal is taken out, from the connection point of resistors $r_{n3}$ and $r_{n4}$, $G_n$ signal, and from the connection point of resistors $r_{n5}$ and $r_{n6}$, $B_n$ signal. The resistor division ratio of the series resistor circuit in the RGB decoders $DC_1$-$DC_n$ differs from decoder to decoder, and in case a picture in each wavelength region is displayed in a particular expressing color (single color), it is made possible to set the signal ratio of R, G and B for each decoder so that the R, G and B signals which make it possible to issue the expressing color. Therefore, for example, if the R, G and B signals from the decoder $DC_1$ are just input to the RGB terminals of the monitor 15 via buffer, etc., image information to correspond to one wavelength region can be displayed in one expressing color. Similarly, if the $R_2$, $G_2$ and $B_2$ signals from the decoder $DC_2$ are just supplied to the monitor 15, the image information corresponding to another wavelength region can be displayed in a color different from the above expressing color. For the $R_n$, $G_n$, and $B_n$ signals from the decoder $DC_n$, too, a different display color can be obtained. In order to select any signal set of $(R_1, G_1, B_1), (R_2, G_2, B_2), \ldots, (R_n, G_n, B_n)$ from the decoders $DC_1$-$DC_n$ and supply it to the monitor 15, the multiplexer 23 is provided inbetween. That is, the multiplexer 23 is provided with the input terminals $T_{R1}$, $T_{G1}$ and $T_{B1}$ for $R_1$, $G_1$ and $B_1$ signals, input terminals $T_{R2}$, $T_{G2}$ and $T_{B2}$ for $R_2$, $G_2$ and $B_2$ signals, and input terminals $T_{Rn}$, $T_{Gn}$ and $T_{Bn}$ for $R_n$, $G_n$, and $B_n$ signals, and by switching in the multiplexer 23, the terminals $T_{R0}$, $T_{G0}$ and $T_{B0}$ are connected to any of the input terminals $(T_{R1}, T_{G1}, T_{B1})$, $(T_{R2}, T_{G2}, T_{B2})$, ..., $(T_{Rn}, T_{Gn}, T_{Bn})$ to display the image information for each wavelength region in single color on the monitor 15. The output terminals $T_{R0}$, $T_{G0}$ and $T_{B0}$ of the multiplexer 23 are connected to the RGB terminals of the monitor 15 via the buffer amplifiers 24, 25 and 26 respectively. The multiplexer 23 is also provided with the input terminals $T_R$, $T_G$ and $T_B$. To the input terminal $T_R$, the $R_1$, $R_2$, ..., $R_n$ signals output from the RGB decoders $DC_1$, $DC_2$, ..., $DC_n$ are added by the adder 27 and input, to the input terminal $T_G$, the $G_1$, $G_2$, ..., $G_n$ signals from the decoders $DC_1$, $DC_2$, ..., $DC_n$ are added by the adder 28 and input, and to the input terminal $T_B$, $B_1$, $B_2$, ..., $B_n$ signals from the decoders $DC_1$, $DC_2$, ..., $DC_n$ are added by the adder 29 and input. Therefore, if the output terminals $T_{R0}$, $T_{G0}$ and $T_{B0}$ are connected to the input terminals $T_R$, $T_G$ and $T_B$ respectively by switching in the multiplexer 23, the picture of each wavelength region can be superimposed on each other and can be displayed in color on the monitor 15.

In case the image signals of each wavelength region stored in the frame memories $M_1$–$M_n$ are read out, if the reading speed is increased several times higher than the normal speed by means of the control signal $S_C$ of the control circuit 22 to read them sequentially and at the same time the switching in the multiplexer 23 is sequentially done for the input terminals $(T_{R1}, T_{G1}, T_{B1})$, $(T_{R2}, T_{G2}, T_{B2})$, ..., $(T_{Rn}, T_{Gn}, T_{Bn})$, the picture can be divided for each wavelength and the divided pictures can be displayed in different colors.

If the image signals of each wavelength stored in the frame memories $M_1$–$M_n$ are sequentially read out by specifying a particular address by means of the control signal $S_C$ of the control circuit 22 and the screen display is made by using that signal, it is also possible to display the reflectance or absorption spectrum waveform of a particular point.

FIG. 6 shows in the concrete one example of the makeup of the spectral characteristic correcting part 12 shown in FIG. 1. The light separated into each wavelength region is received by the light receiving element 9 shown in FIG. 1 or FIG. 2 and converted into electrical signals which are then input to the sample holding circuit 11 via the amplifier 10. The signal sample-held is converted into digital signal by the AD converter 30 and input to the programmable ROM 31. The programmable ROM 31 in which the spectrum correction data are stored in advance can select and output the correction data corresponding to the value of the aforementioned digital input signal. The input/output operation of the ROM 31 is controlled by means of the frame switching signal f correspondingly to each wavelength region. The correction data from the ROM 31 are again converted into analog signals by the DA converter 32 and added to the gain control terminal of the amplifier 8. In the amplifier 8 the gain is automatically controlled for each wavelength region by means of the correction signal obtained from the DA converter 32. Therefore, the strength of the image pickup signals from the image pickup element 7 is corrected to a proper level for each wavelength region.

Figure 7:
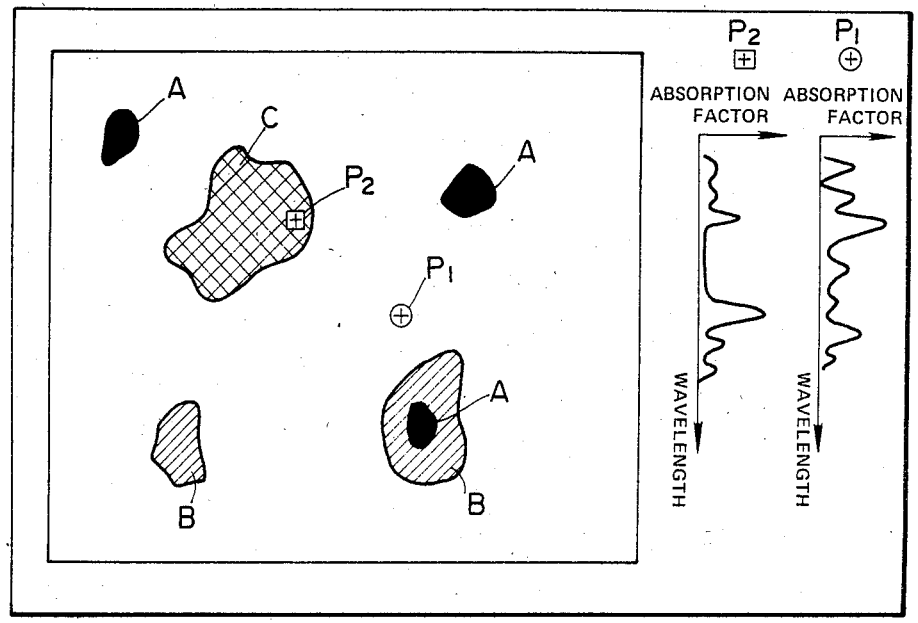
FIG. 7 is a front view to show one example of the picture displayed by the equipment of this invention.
Figure 8:
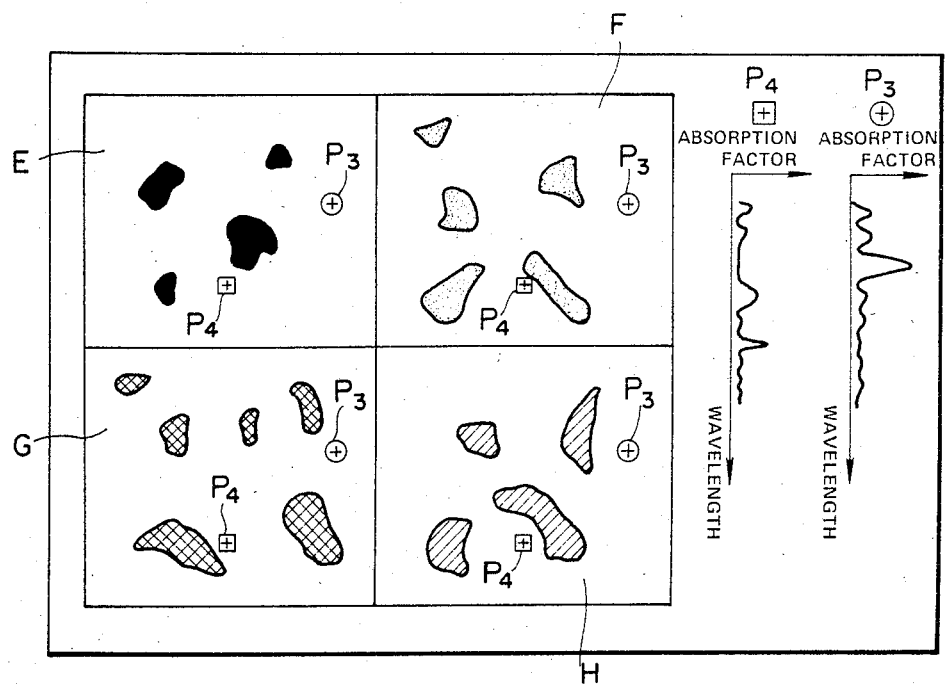
FIG. 8 is a front view to show another example of the picture displayed by the equipment of this invention.

FIGS. 7 and 8 show examples of pictures displayed on the monitor 15. FIG. 7 is a display example showing what was picked up in multiple wavelength regions, synthesized and color-displayed. Each part of the subject has a different reflection or absorption factor against each wavelength, and Part A picked up in one wavelength region and Parts B and C picked up in different wavelength regions can be displayed together. Shown on the right hand side are the spectral analysis waveforms to show the absorption spectrum at $P_1$ and $P_2$ points in the displayed picture. FIG. 8 shows divided screens to show what was picked up in multiple wavelength regions and 4 pictures E, F, G and H taken in 4 wavelength regions are separately displayed in color. Shown on the right hand side of this figure are spectral analysis waveforms as in the case of FIG. 7, and these waveforms show the absorption spectrum at Points $P_3$ and $P_4$. As aforementioned, if the information obtained by illuminating a subject in the light of different wavelength regions is stored in the frame memory for each wavelength, and read and processed as required, it is possible to display in color the pictures in different wavelength regions in superimposed way or to divide the screen and display the pictures in different wavelength regions on the divided screens in different colors and also to display in waveform the absorption spectrum at a particular point. On basis of these analyzed information, it is possible to discriminate the affected part and normal part and to find abnormality such as morbid part easily and quickly.

In the above embodiment, the light source lamp 1 radiates the light including a wide range of wavelength region from infrared region to visible region and ultraviolet region, but it is also possible to use multiple luminous diodes with different wavelength regions in place of the light source lamp 1.

It is clear that many other embodiments can be formed on basis of this invention without deviating from the spirit and scope of this invention. This invention is not limited to the particular embodiments except the limitations stated in the claims.

We claim:

1. Endoscope equipment consisting of an illuminating means to irradiate in time series the light separated into multiple wavelength regions to illuminate a subject, image pickup element to receive the light reflected from the subject and convert it into electrical signals, light receiving element having the same characteristics as the image pickup element to receive the light separated into multiple wavelength regions and convert it into electrical signals, correcting means to control the electrical signals from the aforementioned image pickup element on basis of the electrical signals obtained at the light receiving element and correct the spectral characteristics, signal processing means to process the electrical signals corrected by the correcting means for each wavelength regions and produce the signals for screen display, and display means to display the picture in each wavelength region using the signals from the signal processing means and by means of a particular color signal and display are spectral waveform.

2. The equipment described in claim 1 and characterized in that the said correcting means consists of a correction signal forming circuit to produce spectral characteristic correcting signals on basis of the electrical signals obtained at the light receiving element and a variable gain amplifier circuit to amplify the electrical signals from the aforementioned image pickup element and also to automatically control the gain using the correction signal from the aforementioned correction signal forming circuit.

3. The endoscope equipment described in claim 2 and characterized in that the said correction signal forming circuit consists of a sample holding circuit to sample-hold the electrical signals obtained at the aforementioned light receiving element, A/D converter circuit to convert the sample-held signals into digital signals, memory circuit to input the said digital signals and select and output the spectrum correction data corresponding to the value, and D/A converter circuit to convert the said spectrum correction data output from the circuit into analog signals and supply them to the aforementioned variable gain amplifier circuit.

4. The endoscope equipment described in claim 1 and characterized in that the said signal processing means consists of a switching circuit to switch and output the electrical signals corrected through the aforementioned correcting means in accordance with the aforementioned wavelength region, multiple signal holding circuits to sequentially accumulate the electrical signals from the switching circuit for each wavelength region, and signal processing circuit to read the accumulated electrical signals as required from the multiple signal holding circuits and produce the signals for screen display.

5. Endoscope equipment described in claim 4 and characterized in that the said signal processing circuit consists of a control circuit to control the reading of signals from the aforementioned multiple signal holding circuits, mutiple digital/analog converter circuits to the signals for each wavelength region read from the multiple signal holding circuits into analog signals, multiple color signal converter circuit to convert the converted analog signals for each wavelength region into red, green and blue signals of the ratio corresponding to the expressing colors for each wavelength region, 3 addition circuits to synthesize the color signals of the particular colors converted for each wavelength region per red, green or blue signal, and switching circuit to switch the red, green and blue signals obtained from the 3 adder circuits and the red, green and blue signals for each wavelength region obtained from the multiple color signal converter circuits and supply them to the aforementioned display means.

6. The endoscope equipment described in claim 1 or 4 and characterized in that the said illuminating means consists of a rotary filter with multiple spectral filters with different transmission wavelength regions against irradiation from the light source arranged in a circular form on the same circumference to produce the switching signals for the aforementioned signal holding circuit by detecting the position of the rotary filter corresponding to each spectral filter.

* * * * *